Figure 3A:
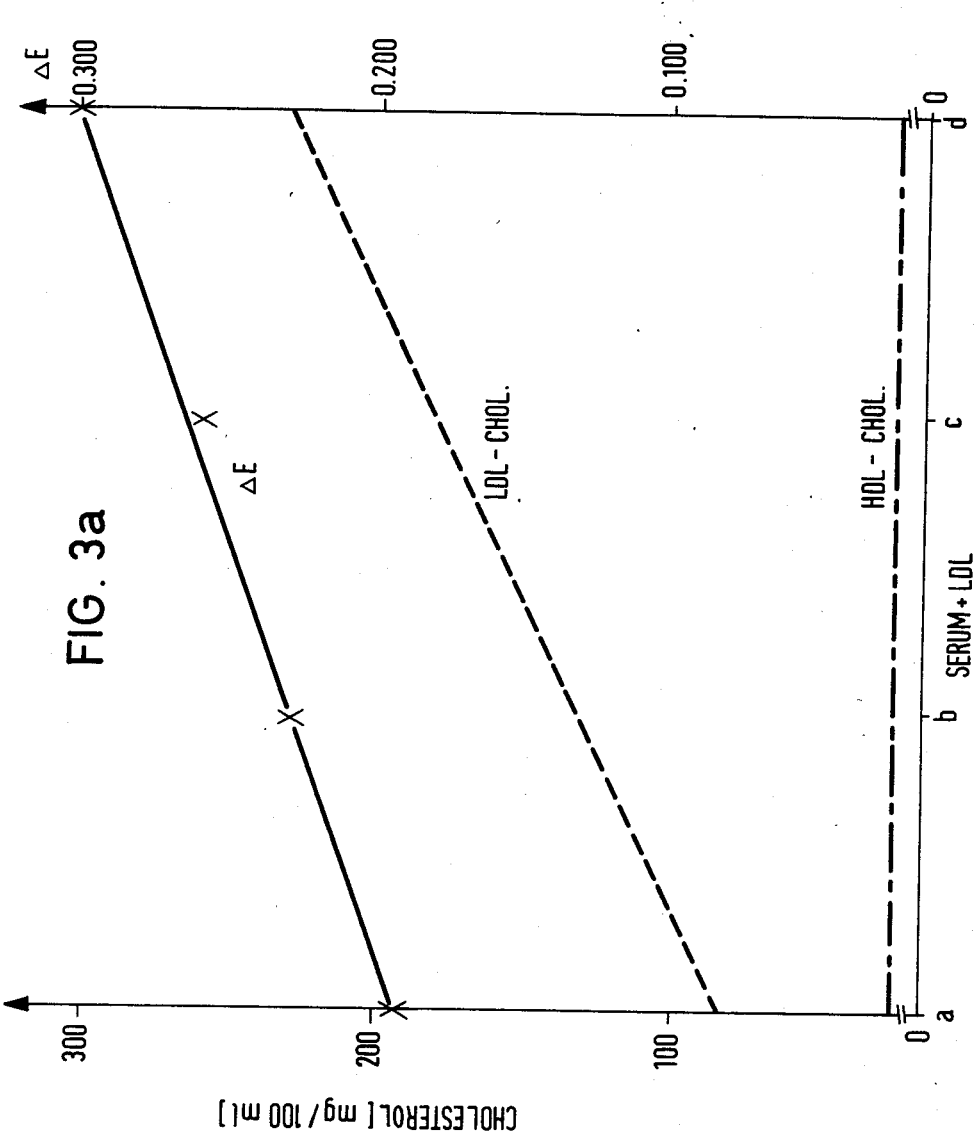

United States Patent [19]

Ziegenhorn et al.

[11] Patent Number: 4,544,630
[45] Date of Patent: Oct. 1, 1985

[54] PROCESS FOR SPECIFIC DETERMINATION OF CHOLESTEROL IN THE PRESENCE OF THE HDL FRACTION IN SERUM

[75] Inventors: Joachim Ziegenhorn, Starnberg; Albert Röder, Seeshaupt; Knut Bartl, Wilzhofen; Gunter Wehmeyer, Starnberg, all of Fed. Rep. of Germany

[73] Assignee: Boehringer Mannheim GmbH, Mannheim-Waldhof, Fed. Rep. of Germany

[21] Appl. No.: 468,792

[22] Filed: Feb. 22, 1983

[30] Foreign Application Priority Data

Mar. 8, 1982 [DE] Fed. Rep. of Germany ....... 3208253

[51] Int. Cl.⁴ .......................... C12Q 1/60; C12Q 1/44
[52] U.S. Cl. ........................................ 435/11; 435/11; 435/19; 436/71
[58] Field of Search ....................... 435/11, 19; 436/71

[56] References Cited

U.S. PATENT DOCUMENTS 4,226,713 10/1980 Goldberg .................. 436/71

Primary Examiner—Sidney Marantz
Assistant Examiner—Stephen C. Wieder
Attorney, Agent, or Firm—Felfe & Lynch

[57] ABSTRACT

The present invention provides a process for the specific determination of the cholesterol of the LDL fraction in the presence of the HDL fraction of the lipoproteins of serum by the action of cholesterol esterase for the liberation of the cholesterol and oxidation of the liberated cholesterol with cholesterol oxidase and oxygen with the formation of hydrogen peroxide and cholestenone and kinetic measurement of the change of one of the reaction components of the oxidase reaction, especially the formation of hydrogen peroxide, wherein the measurement is carried out in a predetermined period of time, the reaction solution having a tenside concentration of 0.01 to 1.5 mmol/liter, a cholesterol esterase concentration of 0.1 to 30 U/ml. and a pH value of 6.5 to 8.0.

The present invention also provides a reagent for carrying out this process.

15 Claims, 6 Drawing Figures

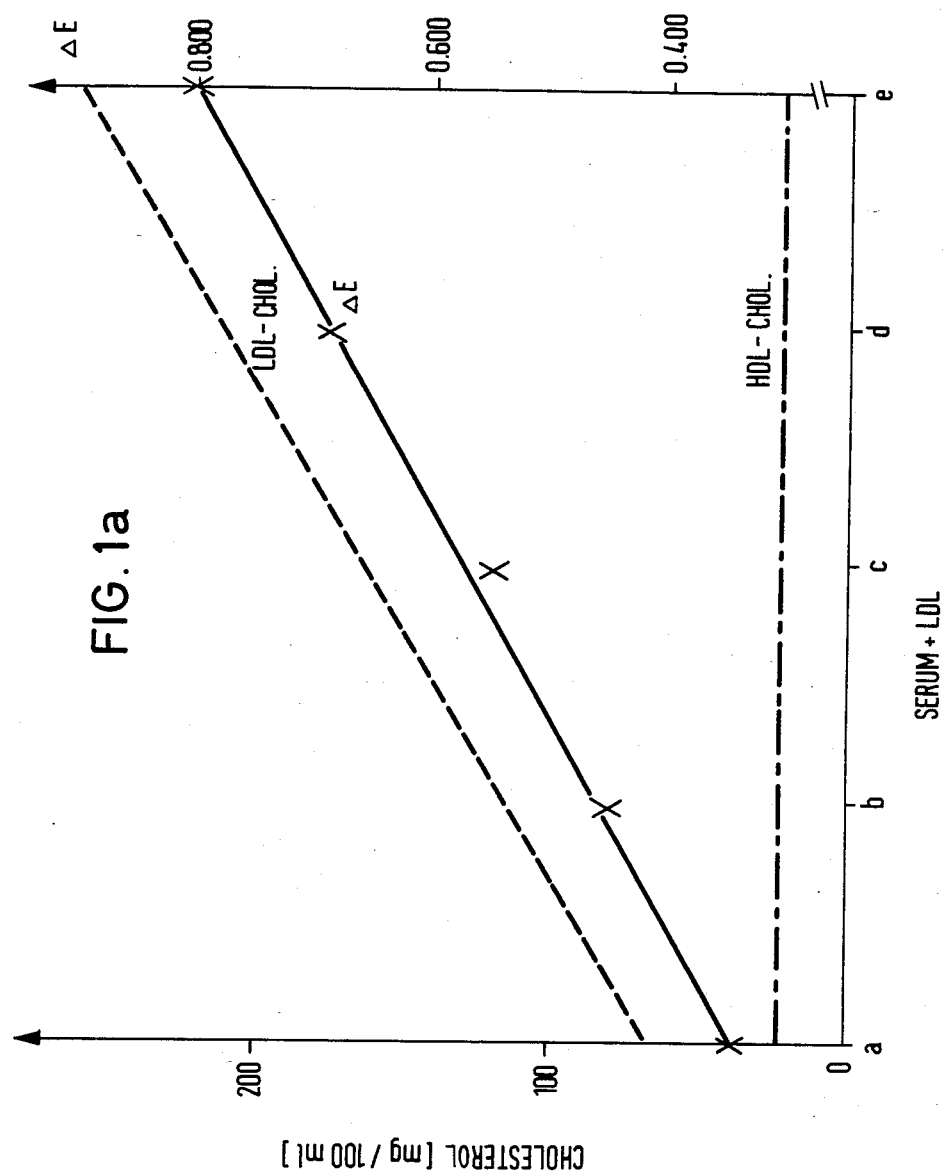

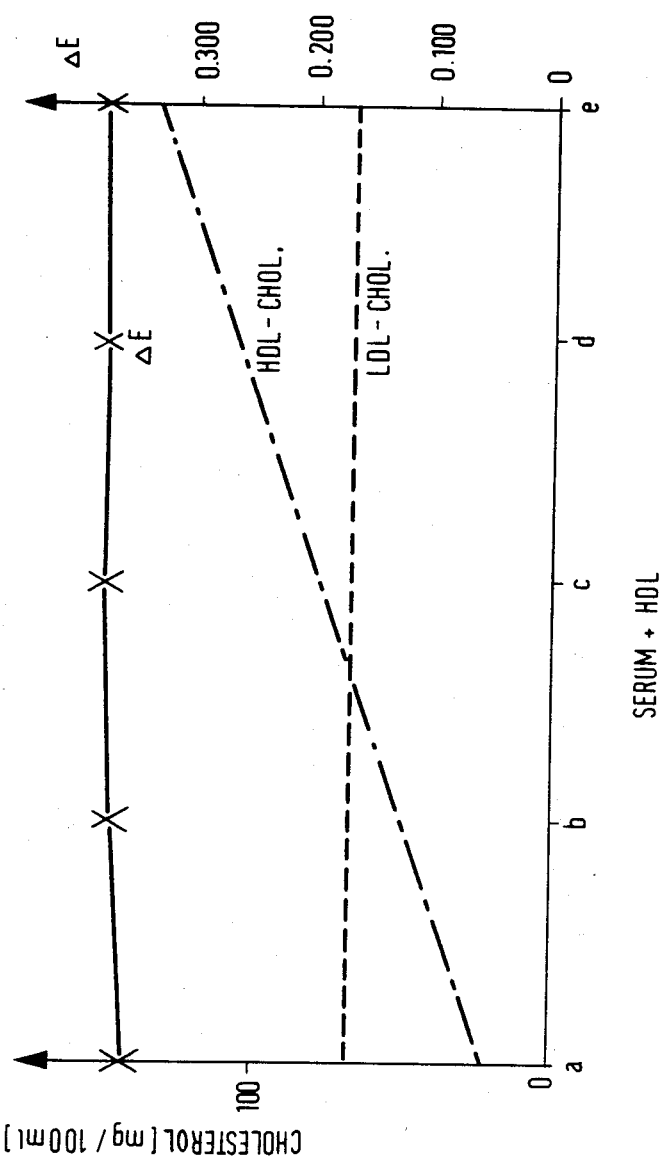

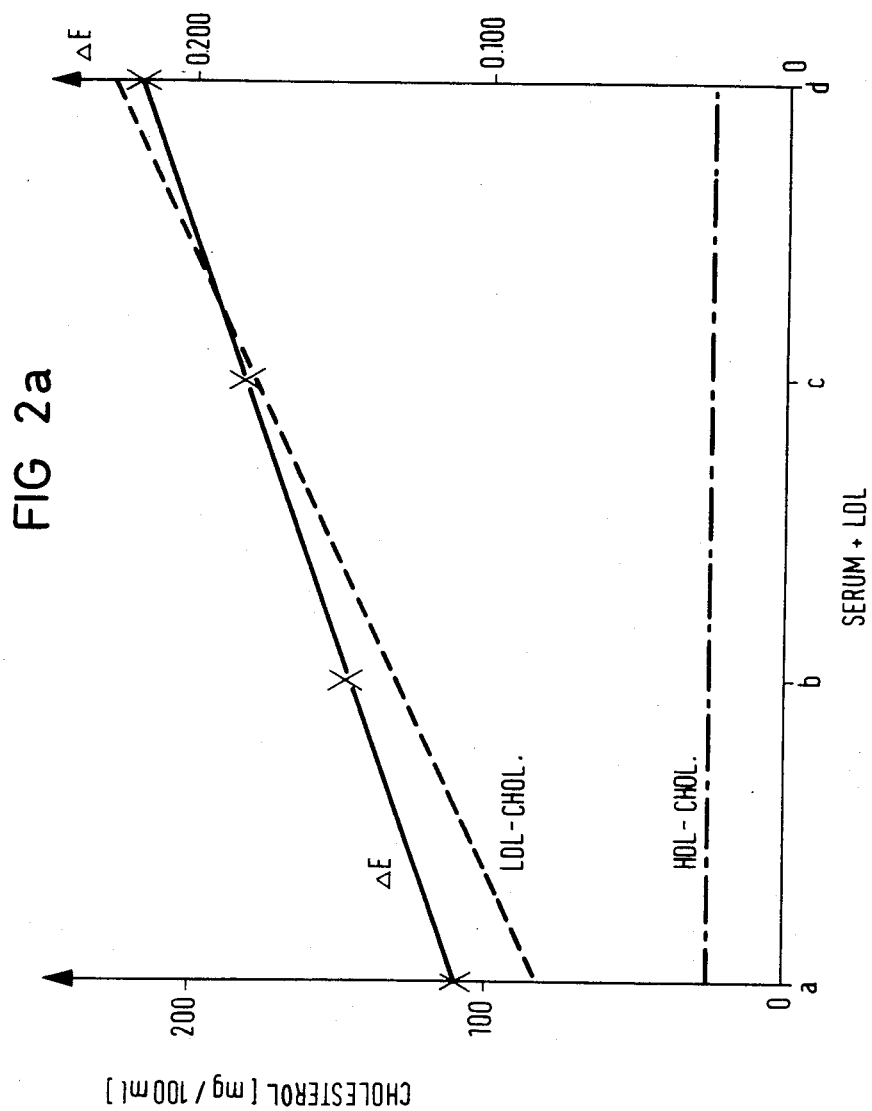

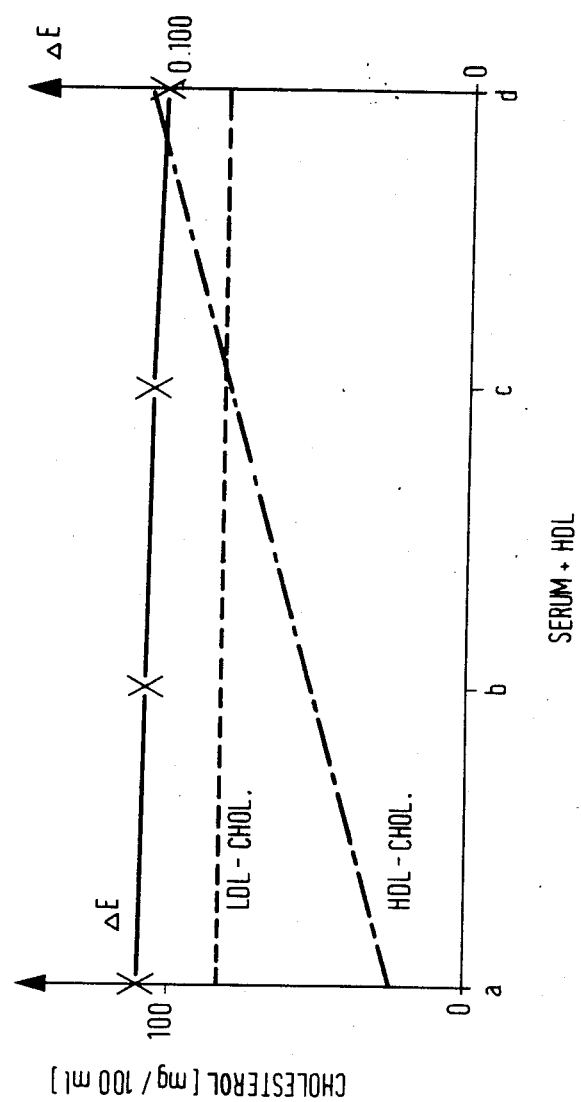

PROCESS FOR SPECIFIC DETERMINATION OF CHOLESTEROL IN THE PRESENCE OF THE HDL FRACTION IN SERUM

The present invention is concerned with a process and a reagent for the specific determination of the cholesterol of the LDL fraction in the presence of the HDL fraction of serum lipoproteins.

The determination of the LDL fraction (low density lipoprotein), also called the β-lipoprotein fraction, is of considerable importance for the differentiated diagnosis of a disturbance of the metabolism of lipid materials.

Hypercholesterolaemia and hypertriglyceridaemia favour the genesis of atherosclerosis and of heart infarct. Therefore, the determination of cholesterol and triglycerides in the serum belong to the most frequently carried out tests in routine clinical-chemical laboratories.

Numerous investigations of the fat metabolism have resulted in the conclusion that the individual coronary risk can be better predicted when a determination is made not only of the triglyceride and cholesterol levels but also of the fundamental pathological displacements in the lipoprotein pattern (see Münch. med. Wochenschrift, 121, 1639/1979).

The known plasma lipoproteins contain varyingly high proportions of proteins, phospholipids, cholesterol and triglycerides. On the basis of their behaviour (differing density) in an analytical unltracentrifuge, they can be subdivided into three different classes:

pre-β-lipoproteins = VLDL (very low density lipoprotein)
β-lipoprotein = LDL (low density lipoprotein)
α-lipoprotein = HDL (high density lipoprotein).

Investigation of the function of the lipoproteins demonstrated that, of the lipoproteins, LDL represents the decisive atherogenic component, an increase of which in the blood representing an increased risk of a coronary heart disease. Therefore, the early recognition and combating of this condition is of great importance. Consequently, there is a need for a practical process for the quantitative determination of the LDL concentration in the serum and plasma.

Hitherto, essentially four methods have been used for the determination of the LDL protein fraction which, nevertheless, possess disadvantages:

1. Ultracentrifuging

This process is not suitable for a routine laboratory because carrying it out requires a special equipment of the apparatus, an extremely careful working technique and a very high expenditure of time (for centrifuging for several days in an ultracentrifuge). Consequently, this method has hitherto been restricted to medical research laboratories.

2. Precipitation reaction

The LDL content can also be determined by a fractional precipitation with a polyanion, such as heparin sodium or dextran sulphate, and a divalent cation, such as calcium, manganese or magnesium. In this case, the lipoproteins can be precipitated with increasing concentration of the polyanion in the following sequence: VLDL, LDL and HDL. However, this process requires two working steps and thus is impracticable and not capable of automation: VLDL is separated off in a first precipitation step and subsequently, by increasing the concentration of the precipitation agent, the LDL lipoprotein fraction is precipitated and measured turbidmetrically (see H. Okabe, Xth Int. Congr. of Clin. Chem., Mexico, 1978).

3. Determination of the LDL concentration via the Friedewald formula

In the case of this process, there is determined the triglyceride and complete cholesterol content, as well as the HDL cholesterol content of the sample by precipitating out VLDL and LDL and the content of LDL cholesterol is calculated therefrom by Friedewald's formula (see Clin. Chem., 18, 499/1972). However, this laborious process is also impracticable.

4. Electrophoretic separation and polyanion precipitation

However, this process is time-consuming and requires the use of an electrophoresis apparatus, as well as of a densitometer, for evaluation (see Lab. Med., 1, 145/1977).

A process which avoids the above-described disadvantages is described in Federal Republic of Germany Patent Specification No. 30 07 764.6. This process depends upon the direct turbidimetrical determination of the LDL fraction in body fluids by precipitation with a polyanion and a divalent cation from aqueous solution, the precipitation being carried out in the presence of a complex former at a pH value of from 7 to 9. This process admittedly provides a considerable technical advance in comparison with the above-mentioned older processes and, in particular, can be automated so that it can be used in a routine laboratory. However, since it is absolutely essential to carry out a turbidimetric determination, for which not all laboratories are equipped, there is still a need for a simplified process which can be carried out as a colour test not only with conventional photometers but also with automatic analysers.

An advantage of the process according to the present invention is that, in contradistinction to the LDL total particle, in the case of LDL cholesterol, a parameter is determined upon the quantification of which the previous epidemiological investigations have been preponderantly based.

Therefore, for this parameter, more dependable "normal values" are available than for the LDL content or HDL content as a whole. Therefore, hitherto for the determination of the cholesterol content in the LDL fraction, the latter had first to be isolated and then the cholesterol determined in a separate step. The direct determination of the cholesterol in the LDL fraction without previous fraction separation is, therefore, not only desired for reasons of practicability but also gives directly the parameter which provides the best predictions.

Therefore, it is an object of the present invention to provide a process which, without a precipitation reaction and without fraction separation, permits a direct enzymatic determination of the cholesterol present in the LDL fraction and which can also be carried out as a colour test.

This object is achieved according to the present invention by a process which utilizes the surprising effect that, under certain conditions, the enzymatic determination of the proportion of cholesterol present in the lipoproteins in the LDL fraction proceeds substantially more quickly than in the HDL fraction.

The process according to the present invention for the specific determination of the cholesterol of the LDL fraction in the presence of the HDL fraction of the lipoproteins of the serum by the action of cholesterol esterase for the liberation of the cholesterol and oxidation of the liberated cholesterol with cholesterol oxidase and oxygen with the formation of hydrogen peroxide and cholestenone and kinetic measurement of the change of one of the reaction components of the oxidase reaction, especially the formation of hydrogen peroxide, is, therefore, characterised in that the measurement is carried out in a predetermined interval of time, the reaction solution having a tenside concentration of from 0.01 to 1.5 mmol/liter, a cholesterol esterase concentration of from 0.1 to 30 U/ml. and a pH value of from 6.5 to 8.0.

Thus, the present invention depends upon precisely correlated concentration ratios of tensides and cholesterol esterases and upon a definite pH value.

Under the above-described conditions, the enzymatic determination of the cholesterol proportion in the HDL fraction proceeds, surprisingly, with a constant velocity up to about 150 mg./100 ml. independently of the HDL concentration (normal range 35 to 55 mg./100 ml.), whereas the reaction velocity of the cholesterol proportion in the LDL fraction depends linearly upon its concentration. In the case of a kinetic measurement, the measurement value thereby obtained is directly proportional to the LDL cholesterol concentration in the reaction mixture.

The determination of free cholesterol by means of cholesterol oxidase, with the formation of hydrogen peroxide and cholestenone and the kinetic determination of the change of one of the reaction components of this oxidation reaction, is known, for example, from Federal Republic of Germany Patent Specification No. 25 58 536. As the measurement parameter, there can thereby be used not only the decrease of the oxygen concentration but also the formation of cholestenone or of hydrogen peroxide. Hydrogen peroxide formed is preferably determined, using colorimetric methods known for the determination of hydrogen peroxide. A typical method for the determination of hydrogen peroxide, which is especially suitable for the present invention, depends upon the colour reaction of phenol or a phenol derivative with 4-aminoantipyrine or a derivative thereof in the presence of peroxidase. These determinations are well known and do not need to be described here in detail.

The cholesterol oxidase used can be any of the commercially available preparations, for example one obtained from *Nocardia erythropoles*. This also applies to the cholesterol esterase, cholesterol esterase preparations from Pseudomonas or Candida strains being preferred. Such enzyme preparations are known and commercially available.

The kinetic carrying out of the measurement in a predetermined interval of time is important for the present invention, as is the maintenance of a definite tenside concentration, of a definite cholesterol esterase activity and of a definite pH range.

In principle, within the scope of the present invention, use can be made of tensides from the known groups, namely, the non-ionic, the cationic, the anionic and the bile acid derivatives. However, the individually optimum concentrations in these groups differ somewhat and, in the case of the bile acid derivatives and of the cationic tensides, it is also preferred to work within a special and narrower pH value range.

In the case of the non-ionic tensides, which are essentially the alkyl and alkyl aryl esters and ethers of polyethylene oxides, the preferred concentration range is from 0.01 to 0.3 mmol/liter, the range of from 0.06 to 0.18 mmol/liter being especially preferred.

In the case of the anionic tensides, for example sodium dioctylsulphosuccinate, the preferred concentration is from 0.01 to 0.70 mmol/liter and especially from 0.05 to 0.35 mmol/liter.

In the case of the bile acid derivatives, which can be included with the anionic tensides, the preferred concentration range is especially wide and is from 0.01 to 1.5 and especially from 0.05 to 1.0 mmol/liter. However, in this case, it is preferred to maintain a pH value of from 7.2 to 8.0 and more preferably from 7.6 to 8.0. The preferred bile acid derivatives are the desoxycholates, for example sodium desoxycholate.

In the case of cationic tensides, such as CTAB (cetyl trimethylammonium bromide), the preferred concentration range is from 0.02 to 0.8 mmol/liter, the range of from 0.08 to 0.35 mmol/liter being especially preferred. In this case, it is preferred to maintain a pH value of from 6.5 to 7.6 and more preferably of from 6.8 to 7.2.

Within the scope of the present invention, mixtures of tensides can also be used, for example mixtures of nonionic tensides and tensides of the bile acid group.

For the adjustment of the necessary pH value range, there are, in each case, added the buffer substances effective in the given ranges. With regard to the buffer substances which can be used there are, per se, no limitations but phosphate buffer is preferred and tris/HCl buffer is especially preferred. In general, the buffer concentration can be from about 20 to about 500 mmol/liter, the range of from 50 to 200 mmol/liter being preferred.

The measurement period of time can be relatively wide. However, the measurement is preferably carried out in the range of from 0.5 to 15 minutes after the start of the reaction, whereby, for example, in the case of a colour test, the extinction difference in the measurement interval is determined, thus, for example, the difference between the extinctions 0.5 and 10 minutes after commencement of the reaction. However, the measurement period of time can also be considerably shortened.

For carrying out the process according to the present invention, use can be made of commercially available reagents based upon a content of cholesterol oxidase and cholesterol esterase, insofar as they do not give a pH value outside of the range permissible for the present invention. The chosen tenside is then added to these reagents in the concentration to be used according to the present invention. In the case of the colour reagent already mentioned above, the preferred ranges for the individual components of the reagent are as follows:

100 to 5000 U/liter cholesterol oxidase,
100 to 30,000 U/liter cholesterol esterase,
100 to 5000 U/liter peroxidase,
0.5 to 10 mmol/liter 4-aminoantipyrine,
2 to 20 mmol/liter phenol or phenol derivative, as well as tenside and buffer, as explained above in more detail.

A preferred reagent according to the present invention contains:

200 to 1000 U/liter cholesterol oxidase,
100 to 3000 U/liter peroxidase,
2000 to 10,000 U/liter cholesterol esterase,
0.10 to 0.16 mmol/liter of tenside,
5 to 20 mmol/liter phenol,
0.5 to 3 mmol/liter 4-aminoantipyrine,
70 to 130 mmol/liter tris/HCl (pH 7.3 to 7.7).

The present invention makes it possible to determine directly the most interesting parameter, namely, the cholesterol content in the LDL fraction, without previous separation of the lipoprotein fractions, without precipitation reactions and without centrifuging. The process can be carried out simply and quickly and specifically determines only the cholesterol in the LDL fraction in the presence of the HDL fraction.

The following Examples are given for the purpose of illustrating the present invention. The Examples were all carried out with the use of a GEMSAEC automatic analyser. In order to achieve comparability, the reactions were all carried out in 100 mmol/liter tris/HCl buffer (pH 7.5) containing 600 U/liter cholesterol oxidase, 2000 U/liter peroxidase, 10 mmol/liter phenol and 1 mmol/liter 4-aminoantipyrine.

EXAMPLE 1

Fresh human serum was mixed with physiologically acceptable sodium chloride solution and various amounts of LDL. The amounts added varied, but the relative proportions remained the same. Upon addition of the LDL and NaCl, the serum was diluted by 50%. The LDL fraction was then obtained by ultracentrifugation of the mixture and isolation of the appropriate bands.

To the so obtained serum supplemented with LDL there were added the above-mentioned amounts of cholesterol oxidase, peroxidase, phenol and 4-aminoantipyrine, as well as tris/HCl. Furthermore, there were added cholesterol esterase from Pseudomonas in an amount of 10 U/ml. and the anionic tenside Aerosol OT (American Cyanamid) in an amount of 0.11 mmol/liter. The extinction was then measured after 0.5 minutes and after 10 minutes. FIG. 1a of the accompanying drawings graphically represents the results obtained. It can be seen from this that there is a linear correlation between the measurement value and the concentration of the LDL cholesterol. In this FIG., the cholesterol concentration is given on the left in mg. per 100 ml. and the extinction difference is given on the right.

The above-described experiment was repeated but the human serum was not supplemented with an LDL fraction but with an HDL fraction, whereby, because of the considerably lower HDL concentration in the serum, other concentration relationships were chosen. The results obtained are illustrated graphically in FIG. 1b of the accompanying drawings. It can be seen that there is no linear correlation between the measurement value and the concentration of HDL cholesterol but that the extinction difference corresponds to the LDL content of the starting serum.

EXAMPLE 2

The procedure described in Example 1 was used. The content of cholesterol esterase was 10 U/ml. As tenside, there was added sodium desoxycholate in a concentration of 0.10 mmol/liter.

The results obtained with the mixture supplemented with LDL fraction are shown in FIG. 2a of the accompanying drawings. A linear correlation between the measurement value and LDL cholesterol concentration can again be seen.

The results obtained when repeating the experiment with a human serum supplemented with HDL are illustrated in FIG. 2b of the accompanying drawings. It can be seen that, here again, the measurement values have a linear correlation with the LDL concentration (this concentration was the same in all samples and corresponded to the content of the 1:1 diluted serum for originally present LDL), whereas there was no correlation with the HDL concentration.

EXAMPLE 3

The procedure described in Example 1 was used. The cholesterol esterase content in the measurement solution was 2 U/ml. As tenside, the cationic cetyl trimethylammonium bromide was added in a concentration of 0.166 mmol/liter. The results obtained in the case of human serum supplemented with LDL are graphically illustrated in FIG. 3a of the accompanying drawings. Here, too, a linear correlation can be seen between the measurement value and the LDL cholesterol concentration.

Figure 3B:
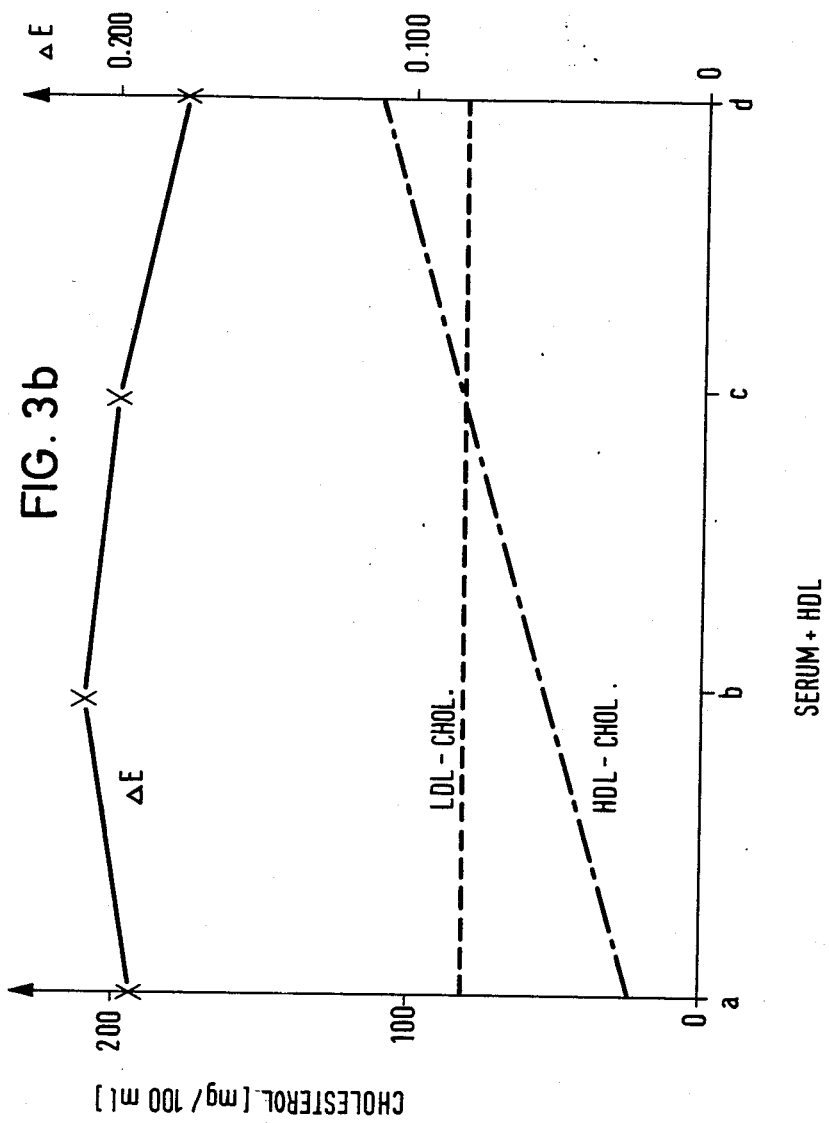

The results obtained with human serum supplemented with HDL are graphically illustrated in FIG. 3b of the accompanying drawings. It can again be seen that there is no correlation between the HDL content and the measurement value which, with a variation of about 8%, is constant and corresponds to the amount of LDL originally present in the serum.

EXAMPLE 4

The differing reaction of the LDL and HDL fraction is made clear by the following Example. Use was made of the reagent mixture described in Example 3 with the same tenside and the same tenside concentration and with a cholesterol esterase concentration of 10 U/ml. To two different batches of this reagent mixture were added equal amounts of an isolated LDL fraction with a concentration of 385 mg. cholesterol per deciliter or of an HDL fraction with a concentration of 226 mg. cholesterol per deciliter.

The extinction difference obtained with the LDL fraction was 0.3259 which, recalculated for 226 mg. per deciliter, equals 0.1934. In the case of the serum supplemented with HDL, the extinction difference was 0.0176. From this is calculated the ratio $LDL_{226}/HDL_{226} = 1:10$.

We claim:

1. A process for specific determination of cholesterol present in the LDL serum fraction, in the presence of an HDL fraction of serum lipoproteins, comprising:
    (a) adding a serum sample to cholesterol esterase;
    (b) oxidizing cholesterol thus produced with cholesterol oxidase and oxygen, so as to form hydrogen peroxide and cholestenone, and
    (c) measuring kinetically the concentration of one of the components of (b), wherein said measurement is carried out in a predetermined period of time, so as to provide data allowing elimination of cholesterol background contributed by said HDL fraction.

2. Process according to claim 1, wherein a non-ionic tenside is added in a concentration of 0.01 to 0.30 mmol/liter.

3. Process according to claim 2, wherein the non-ionic tenside concentration is 0.06 to 0.18 mmol/liter.

4. Process according to claim 1, wherein a tenside of the bile acid group is added in a concentration of 0.01 to 1.5 mmol/liter and a pH value of from 7.2 to 8.0 is maintained.

5. Process according to claim 4, wherein the tenside concentration is 0.05 to 1.10 mmol/liter and the pH value is maintained at 7.6 to 8.0.

6. Process according to claim 1, wherein a cationic tenside is used in a concentration of 0.02 to 0.80 mmol/liter and the pH value is maintained at 6.5 to 7.6.

7. Process according to claim 6, wherein the tenside concentration is 0.08 to 0.35 mmol/liter and the pH value is maintained at 6.8 to 7.2.

8. Process according to claim 1, wherein an anionic tenside is used in a concentration of 0.01 to 0.70 mmol/liter.

9. Process according to claim 8, wherein the anionic tenside concentration is 0.05 to 0.35 mmol/liter.

10. Process according to claim 1, wherein the measurement is carried out within a period of 0.5 to 15 minutes after the start of the reaction.

11. Process according to claim 1, wherein cholesteroloxidase from *Nocardia erythropolis* is used.

12. Process according to claim 1, wherein a cholesterol esterase from Candida or Pseudomonas is used.

13. Process according to claim 1 for the specific determination of the cholesterol of the LDL fraction in the presence of the HDL fraction of the lipoproteins of the serum, substantially as hereinbefore described and exemplified.

14. Reagent for carrying out the process according to claim 1, wherein it contains:
  200 to 1000 U/liter cholesterol oxidase,
  1000 to 3000 U/liter peroxidase,
  2000 to 10,000 U/liter cholesterol esterase,
  0.10 to 0.16 mmol/liter of tenside,
  2 to 20 mmol/liter phenol,
  0.5 to 3 mmol/liter 4-aminoantipyrine,
  70 to 130 mmol/liter tris/HCl (pH 7.3 to 7.7).

15. The process of claim 15, wherein the reaction solution has tenside concentration of 0.01 to 1.5 mmol/liter, cholesterol esterase concentration of 0.1 to 30 U/ml, and a pH of from about 6.5 to about 8.0.

* * * * *

UNITED STATES PATENT AND TRADEMARK OFFICE
CERTIFICATE OF CORRECTION

PATENT NO. : 4,544,630
DATED : October 1, 1985
INVENTOR(S) : Joachim Ziegenhorn et al.

It is certified that error appears in the above-identified patent and that said Letters Patent is hereby corrected as shown below:

In The Abstract line 1, delete "The present invention provides a" and insert -- A --.

line 16, delete The present invention also provides" and insert -- Also --.

Claim 15, line 1, "15" should read -- 1 --.

Signed and Sealed this

Thirteenth Day of May 1986

[SEAL]

Attest:

DONALD J. QUIGG

Attesting Officer     Commissioner of Patents and Trademarks